United States Patent
Ogawa (10) Patent No.: US 6,883,362 B2
(45) Date of Patent: Apr. 26, 2005

(54) ULTRASONIC DIAGNOSTIC APPARATUS AND METHOD OF CHECKING ITS PERFORMANCE

(75) Inventor: Eiji Ogawa, Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 14 days.

(21) Appl. No.: 10/100,040

(22) Filed: Mar. 19, 2002

(65) Prior Publication Data

US 2002/0134133 A1 Sep. 26, 2002

(30) Foreign Application Priority Data

Mar. 21, 2001 (JP) ........................................ 2001-079775

(51) Int. Cl.⁷ .............................................. G01N 29/04
(52) U.S. Cl. ........................................ 73/1.86; 73/643
(58) Field of Search ................................ 73/1.82–1.86, 73/602, 655–657, 643

(56) References Cited

U.S. PATENT DOCUMENTS

| | | | | |
|---|---|---|---|---|
| 4,240,281 A | * | 12/1980 | Lather et al. ................. | 73/1.82 |
| 4,331,021 A | * | 5/1982 | Lopez et al. .................. | 73/1.86 |
| 4,484,820 A | * | 11/1984 | Rosencwaig ................... | 374/6 |
| 4,545,251 A | * | 10/1985 | Uchida et al. ................. | 73/631 |
| 4,572,949 A | * | 2/1986 | Bowers et al. ......... | 250/227.27 |
| 4,633,715 A | * | 1/1987 | Monchalin ................... | 73/657 |
| 4,710,030 A | * | 12/1987 | Tauc et al. ................... | 356/432 |
| 4,928,527 A | * | 5/1990 | Burger et al. ................. | 73/657 |
| 5,257,544 A | * | 11/1993 | Khuri-Yakub et al. ........ | 73/579 |
| 5,615,675 A | * | 4/1997 | O'Donnell et al. ......... | 600/425 |
| 5,689,443 A | * | 11/1997 | Ramanathan ............... | 702/183 |
| 5,756,875 A | * | 5/1998 | Parker et al. ................. | 73/1.86 |
| 5,840,023 A | * | 11/1998 | Oraevsky et al. ........... | 600/407 |
| 6,138,495 A | * | 10/2000 | Paltieli et al. ............... | 73/1.86 |
| 6,234,969 B1 | * | 5/2001 | Chaintreuil et al. ........ | 600/449 |
| 6,238,343 B1 | * | 5/2001 | Madsen et al. ............. | 600/437 |
| 6,363,787 B1 | * | 4/2002 | Carlson et al. ............... | 73/579 |
| 6,370,480 B1 | * | 4/2002 | Gupta et al. ................. | 702/39 |
| 2003/0086535 A1 | * | 5/2003 | Teppaz et al. .............. | 378/207 |

FOREIGN PATENT DOCUMENTS

| | | |
|---|---|---|
| JP | 9-146513 | 6/1997 |
| JP | 9-190170 | 7/1997 |
| JP | 9-212144 | 8/1997 |
| JP | 2000-278721 | 10/2000 |
| JP | 2000-287227 | 10/2000 |

* cited by examiner

Primary Examiner—Hezron Williams
Assistant Examiner—Rose M. Miller
(74) Attorney, Agent, or Firm—Sughrue Mion, PLLC (57) ABSTRACT

An ultrasonic diagnostic apparatus capable of quantitatively checking its performance. The ultrasonic diagnostic apparatus includes: an ultrasonic transmission unit; an ultrasonic reception unit; a signal processing unit for processing detection signals output from the ultrasonic reception unit to generate data; a first storage unit for storing data, which has been obtained by transmitting ultrasonic waves to a predetermined object and receiving ultrasonic echoes, as management data; a second storage unit for storing data, which has been obtained by transmitting ultrasonic waves to the predetermined object and receiving ultrasonic echoes when performance of the ultrasonic diagnostic apparatus is checked, as check data; a comparison unit for generating comparison data on the basis of both the management data and the check data; and an image display unit for displaying an image on the basis of the comparison data.

12 Claims, 6 Drawing Sheets

ULTRASONIC DIAGNOSTIC APPARATUS AND METHOD OF CHECKING ITS PERFORMANCE

BACKGROUND OF THE INVENTION

1. Field of the Invention

The present invention relates to an ultrasonic diagnostic apparatus for transmitting ultrasonic waves to an object to be inspected, receiving ultrasonic echoes reflected from the object and displaying images on the basis of the received ultrasonic echoes. Further, the present invention also relates to a method of checking the performance of such an ultrasonic diagnostic apparatus.

2. Description of a Related Art

The quality of images displayed on an image display unit (for example, CRT, LCD, etc.) of an ultrasonic diagnostic apparatus deteriorates due to various factors. For example, a signal-to-noise ratio of images degrades with the deterioration of an ultrasonic transducer for transmission or reception of ultrasonic echoes, and the quality of the images also degrades with the deterioration of the image display unit.

When such image quality deterioration occurred in a conventional ultrasonic diagnostic apparatus, it was impossible to find out which caused the deterioration, the image display unit or another part inside the ultrasonic diagnostic apparatus, because the condition inside the ultrasonic diagnostic apparatus could not be checked. In that case, it was also impossible to analyze the image quality deterioration quantitatively.

In Japanese Patent Laid-open Publication JP-A-9-190170 (hereinafter referred to also as Reference 1), the applicant discloses an image display method in which image signals are subjected to gradation transformation processing based on predetermined gradation transformation conditions and then displayed on light-emitting display means, the method comprising the steps of detecting the external light level irradiated on the light-emitting display means and changing the gradation transformation conditions so as to obtain a desired gradation on the basis of the detection results. The image display method disclosed in Reference 1, however, can not quantitatively check the image quality deterioration due to various reasons, although it can change the gradation of displayed images as a function of the external light level.

In Japanese Patent Laid-open Publication JP-A-9-146513 (hereinafter referred to also as Reference 2), the applicant discloses an image display method in which image signals are subjected to gradation transformation processing and then displayed on light-emitting display means, the method comprising the steps of detecting the amount of deterioration in brightness of the light-emitting display means and correcting the brightness deterioration of the light-emitting display means on the basis of the detected amount of deterioration.

In Japanese Patent Laid-open Publication JP-A-9-212144 (hereinafter referred to also as Reference 3), the applicant discloses an image display method in which image signals are subjected to gradation transformation processing based on a predetermined gradation transformation table and then displayed on image display means, the method comprising steps of detecting the amount of deterioration of brightness of the image display means and correcting the gradation transformation table on the basis of the detected amount of deterioration so that the brightness deterioration of the image display means can be corrected.

The image display methods disclosed in References 2 and 3, however, can not quantitatively check the image quality deterioration due to various reasons, although they can correct brightness deterioration of the light-emitting display means or image display means.

In Japanese Patent Laid-open Publication JP-A-2000-278721 (hereinafter referred to also as Reference 4), the applicant discloses an image quality checking method for display units, the method comprising the steps of displaying specified test patterns on the screen of a display unit, storing the test patterns as digital data, comparing the stored digital data with reference data previously acquired in the same manner in that display unit and outputting a difference value between both data. The image quality checking method for display units disclosed in Reference 4, however, is not designed to evaluate the image quality affected by any part other than the image display unit of a medical diagnostic apparatus having a display unit, although it can quantitatively and objectively evaluate the quality of images appearing on the display unit.

In Japanese Patent Laid-open Publication JP-A-2000-287227 (hereinafter referred to also as Reference 5), the applicant discloses a sharpness measuring method for display units, the method comprising the steps of displaying rectangular wave test patterns including a plurality of line pairs corresponding to a plurality of frequencies at a fixed position on the screen of a display unit, storing the test patterns as digital data, finding the response corresponding to each frequency from the stored digital data, finding the CTF (contrast transfer function) value of the display unit from the response, and then calculating the MTF (modulation transfer function) value from the CTF value. The sharpness measuring method for display units disclosed in Reference 5, however, is not designed to evaluate the image quality affected by any part other than the image display unit of a medical diagnostic apparatus having a display unit, although it can accurately measure the sharpness of images appearing on the display unit.

SUMMARY OF THE INVENTION

The present invention has been conceived in view of the above problems. It is therefore an object of the present invention to provide a method of quantitatively checking the performance of an ultrasonic diagnostic apparatus and to provide an ultrasonic diagnostic apparatus having such a function.

To solve the above problems, an ultrasonic diagnostic apparatus according to the present invention comprises: ultrasonic transmission means for transmitting ultrasonic waves; ultrasonic reception means for receiving ultrasonic echoes to output detection signals; signal processing means for processing the detection signals output from the ultrasonic reception means to generate data; first storage means for storing data, which has been obtained by transmitting ultrasonic waves to a predetermined object and receiving ultrasonic echoes reflected by the predetermined object, as management data; second storage means for storing data, which has been obtained by transmitting ultrasonic waves to the predetermined object and receiving ultrasonic echoes reflected by the predetermined object when performance of the ultrasonic diagnostic apparatus is checked, as check data; comparison means for generating comparison data on the basis of both the management data stored in the first storage means and the check data stored in the second storage means; and an image display unit for displaying an image on the basis of the comparison data generated by the comparison means.

Further, a method of checking performance of an ultrasonic diagnostic apparatus according to the present invention comprises the steps of: (a) previously storing data, which has been obtained by transmitting ultrasonic waves to a predetermined object and receiving ultrasonic echoes reflected by the predetermined object, as management data; (b) storing data, which has been obtained by transmitting ultrasonic waves to the predetermined object and receiving ultrasonic echoes reflected by the predetermined object when performance of the ultrasonic diagnostic apparatus is checked, as check data; (c) generating comparison data on the basis of both the management data stored at step (a) and the check data stored at step (b); and (d) displaying an image on the basis of the comparison data generated at step (c).

According to the present invention, the performance of the ultrasonic diagnostic apparatus can be checked quantitatively by comparing management data stored in advance with check data obtained when the performance of the ultrasonic diagnostic apparatus is checked.

BRIEF DESCRIPTION OF THE DRAWINGS

The above and other objects, aspects, features and advantages of the present invention will become more apparent from the following detailed description when taken in conjunction with the accompanying drawings, in which.

DESCRIPTION OF THE PREFERRED EMBODIMENTS

An embodiment of the present invention will now be described in detail with reference to the drawings. The same reference numerals are given to identical parts, and explanation thereof is omitted.

Figure 1:
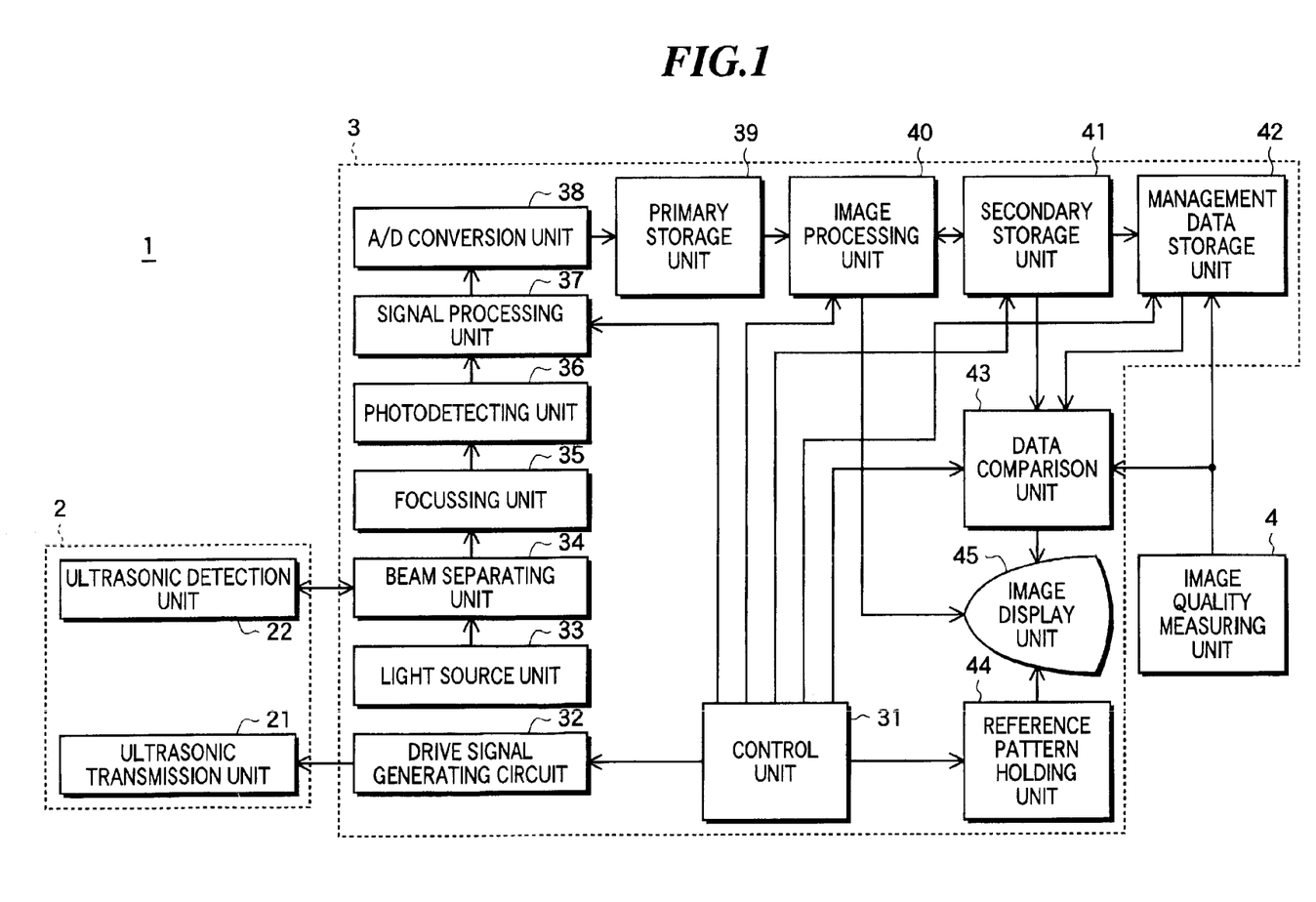
FIG. 1 is a block diagram showing the configuration of an ultrasonic diagnostic apparatus according to one embodiment of the present invention.

FIG. 1 is a block diagram showing the configuration of an ultrasonic diagnostic apparatus according to an embodiment of the present invention. As shown in FIG. 1, the ultrasonic diagnostic apparatus 1 comprises an ultrasonic probe 2, a main unit 3, and an image quality measuring unit 4 for measuring the quality of images displayed by the main unit 3. As the, image quality measuring unit 4, for example, a digital camera or the like can be used to measure the brightness and resolution of displayed images.

The ultrasonic probe 2 comprises an ultrasonic transmission unit 21 including a piezoelectric transducer for transmitting ultrasonic waves to an object to be inspected on the basis of a drive signal sent from the main unit 3, and an ultrasonic detection unit 22 including a light modulation element (ultrasonic detection element) for receiving and modulating light sent from the main unit 3 on the basis of the ultrasonic echoes reflected within the object. Piezoelectric ceramics represented by PZT (Pb(lead) zirconate titanate), high-molecular piezoelectric elements represented by PVDF (polyvinyl difluoride) or the like can be used as the piezoelectric transducer included in the ultrasonic transmission unit 21. The ultrasonic detection unit 22 may include an array of optical fibers to transmit incident light from the main unit 3, and a light modulation element such as FPR (Fabry-Perot resonator) or FBG (fiber Bragg grating) disposed at the end of each optical fiber.

The main unit 3 includes a control unit 31, a drive signal generating circuit 32, a light source unit 33, a beam separating unit 34, a focussing unit 35, a photodetecting unit 36, a signal processing unit 37, an A/D conversion unit 38, a primary storage unit 39, an image processing unit 40, a secondary storage unit 41, a management data storage unit 42, a data comparison unit 43, a reference pattern holding unit 44 and an image display unit 45.

The control unit 31 controls the operation timing for the drive signal generating circuit 32 and the signal processing unit 37 as well as the other units above.

The drive signal generating circuit 32 generates and outputs a drive signal to be used for driving the ultrasonic transmission unit 21 under the control of the control unit 31. The drive signal output from the drive signal generating circuit causes output ultrasonic waves having a specified transmission sound pressure or waveform to the ultrasonic transmission unit 21.

The light source unit 33 generates and emits light having a specified wavelength.

The beam separating unit 34 passes the light emitted from the light source unit 33 toward the ultrasonic detection unit 22, and reflects a part of the incident light from the direction of the ultrasonic detection unit 22 and leads it toward the focussing unit 35.

The photodetecting unit 36 includes more than one PD (photodiode), CCD (charge coupled device) or the like for converting received light into an electric signal.

The focussing unit 35 forms images on the detection surface of the photodetecting unit 36 by focusing incident light from the beam separating unit 34.

The signal processing unit 37 conducts specified signal processing such as demodulation processing on signals output from the photodetecting unit 36 under the control of the control unit 31.

The A/D conversion unit 38 converts each analog signal output from the signal processing unit 37 into a digital signal (data).

The primary storage unit 39 stores digital signals output from the A/D conversion unit 38.

The image processing unit 40 generates image signals (image data) by conducting specified image processing such as gradation treatment on digital signals stored in the primary storage unit 39.

The secondary storage unit 41 stores image data generated by the image processing unit 40.

The management data storage unit 42 receives and stores image data stored in the secondary storage unit 41 when the ultrasonic diagnostic apparatus 1 is accumulating management data.

The image display unit 45 displays images on the basis of image data, etc. generated by the image processing unit 40.

When the performance deterioration of the parts other than the image display unit 45 is checked, the data comparison unit 43 generates comparison data on the basis of image data stored in the secondary storage unit 41 and the management data storage unit 42, so that an image indicative of the comparison results is displayed on the image display unit 45. When the deterioration of image quality due to the image display unit 45 is checked, the data comparison unit 43 also compares image data obtained by imaging the reference pattern by using the image quality measuring unit 4 with image data stored in advance in the management data storage unit 42 by imaging the reference pattern by using the image quality measuring unit 4, so that an image indicating the comparison results is displayed on the image display unit 45.

Figure 2:
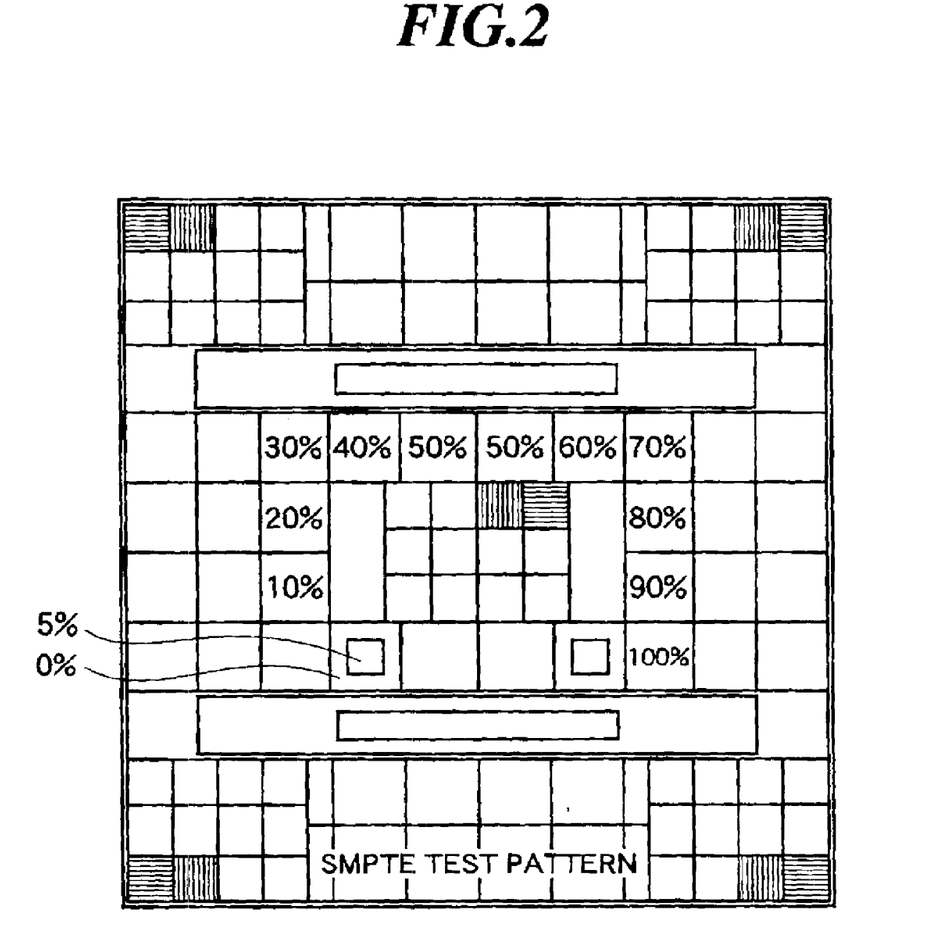
FIG. 2 is a diagram showing an SMPTE pattern.

The reference pattern holding unit 44 holds image data indicating the reference pattern that serves as a reference for checking the deterioration of image quality. The reference pattern includes, for example, a low-contrast pattern or a step pattern used to check the deterioration of brightness, or a resolution measurement pattern used to measure the deterioration of resolution. In this embodiment, an SMPTE pattern is used as the reference pattern. The SMPTE pattern is a pattern as shown in FIG. 2, recommended as a test pattern for medical image quality control by the Society of Motion Picture and Television Engineers, an American society, and ratified by the North American Radiation Society.

Description will then be made about operations of the ultrasonic diagnostic apparatus according to this embodiment of the present invention. The ultrasonic diagnostic apparatus can perform (1) normal imaging operation for normal ultrasonic diagnosis, (2) management data accumulation operation of obtaining and storing management data that serves as a reference for checking performance of the ultrasonic diagnostic apparatus, and (3) performance checking operation of checking performance of the ultrasonic diagnostic apparatus. These operations can be changed over from one to another under control of the control unit in accordance with instructions of an operator.

The normal imaging operation will first be described with reference to FIG. 1.

The ultrasonic diagnostic apparatus starts the normal imaging operation when an operator holds the ultrasonic probe 2 of the ultrasonic diagnostic apparatus so that it is positioned opposite to an object, and gives the ultrasonic diagnostic apparatus a command to start the normal imaging operation.

In the normal imaging operation, the drive signal generating circuit 32 transmits a drive signal to the ultrasonic transmission unit 21 under the control of the control unit 31, and then, the ultrasonic transmission unit 21 transmits ultrasonic waves to an object to be inspected in accordance with the drive signal. The ultrasonic waves transmitted from the ultrasonic transmission unit 21 are reflected by internal organs, etc. within the object and are received by the ultrasonic detection unit 22.

In the ultrasonic detection unit 22, light having a specified wavelength generated by the light source unit 33 is reflected by the light modulation element contained in the ultrasonic detection unit 22 and is modulated by the received ultrasonic echoes. The direction in which the modulated light travels is changed by the beam separating unit 34, and the light passes through the focussing unit 35 and forms an image on the detection surface of the photodetecting unit 36.

The photodetecting unit 36 converts the light received on the detection surface into an analog electric signal. The signal processing unit 37 conducts the specified signal processing on the analog electric signal output from the photodetecting unit 36. The A/D conversion unit 38 generates a digital signal from the analog electric signal output from the signal processing unit 37. The primary storage unit 39 stores the digital signal generated by the A/D conversion unit 38. The image processing unit 40 prepares image data by conducting the specified image processing on the digital signal stored in the primary storage unit 39. The image display unit 45 displays ultrasonic images of internal organs, etc. within the object on the basis of the image data prepared by the image processing unit 40.

Figure 3:
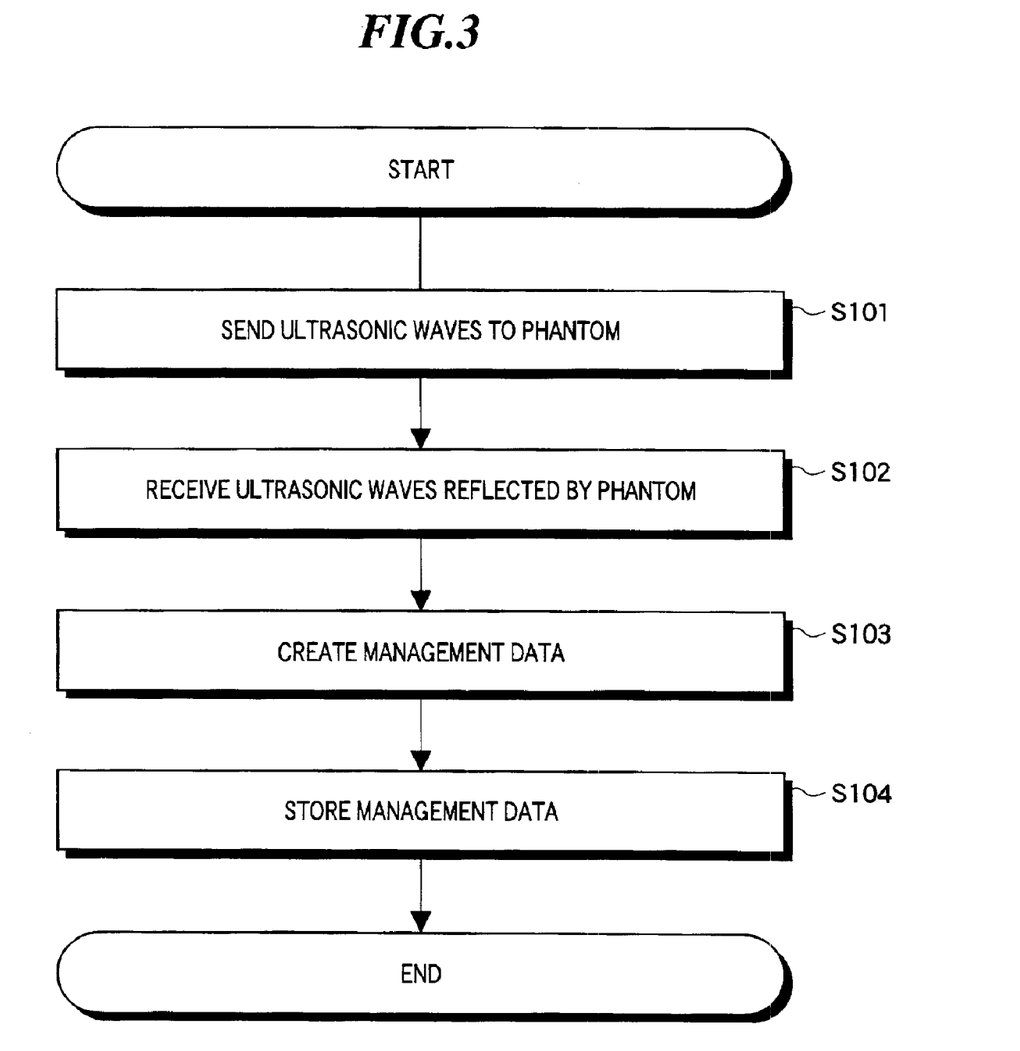
FIG. 3 is a flowchart showing the management data accumulation operation of the ultrasonic diagnostic apparatus according to the embodiment of the present invention.

The management data accumulation operation of the ultrasonic diagnostic apparatus will then be described with reference to FIGS. 1 and 3. FIG. 3 is a flowchart showing the management data accumulation operation of the ultrasonic diagnostic apparatus. The management data accumulation operation is performed, for example, when the ultrasonic diagnostic apparatus 1 is used for the first time. In the management data accumulation operation, a reference object such as a phantom is used to measure the contrast and resolution of ultrasonic images.

The ultrasonic diagnostic apparatus 1 starts a series of management data accumulation operation as shown in FIG. 3 when the operator holds the ultrasonic probe 2 of the ultrasonic diagnostic apparatus 1 so that it is positioned opposite to a phantom, and gives the ultrasonic diagnostic apparatus 1 a command to start the management data accumulation operation.

In the management data accumulation operation, the drive signal generating circuit 32 transmits a drive signal to the ultrasonic transmission unit 21 under control of the control unit 31, the ultrasonic transmission unit 21 transmits ultrasonic waves having the specified transmission sound pressure or waveform to the phantom in accordance with the drive signal (Step S101). The ultrasonic waves transmitted from the ultrasonic transmission unit 21 are reflected by the phantom and are received by the ultrasonic detection unit 22 (Step S102).

In the ultrasonic detection unit 22, light having a specified wavelength generated by the light source unit 33 is modulated by the ultrasonic echoes reflected by the phantom. The direction in which the modulated light travels is changed by the beam separating unit 34, and the light passes through the focussing unit 35 and forms an image on the detection surface of the photodetecting unit 36.

The photodetecting unit 36 converts the light received on the detection surface into an analog electric signal. The signal processing unit 37 conducts the specified signal processing on the analog electric signal output from the photodetecting unit 36. The A/D conversion unit 38 generates a digital signal from the analog electric signal output from the signal processing unit 37. The primary storage unit 39 stores the digital signal generated by the A/D conversion unit 38. The image processing unit 40 prepares image data (hereinafter referred to also as "management data") by conducting the specified image processing on the digital signal stored in the primary storage unit 39. The management data prepared by the image processing unit 40 is stored in the secondary storage unit 41 and also stored in the management data storage unit 42 (Step S103).

It can be assumed that the management data generated as above represents characteristics (initial characteristics) of each part (ultrasonic transmission unit 21, ultrasonic detection unit 22, control unit 31, drive signal generating circuit 32, light source unit 33, beam separating unit 34, focussing unit 35, photodetecting unit 36, signal processing unit 37, A/D conversion unit 38, primary storage unit 39, image processing unit 40, secondary storage unit 41 and management data storage unit 42) of the ultrasonic diagnostic apparatus 1 when the management data is accumulated.

Figure 4:
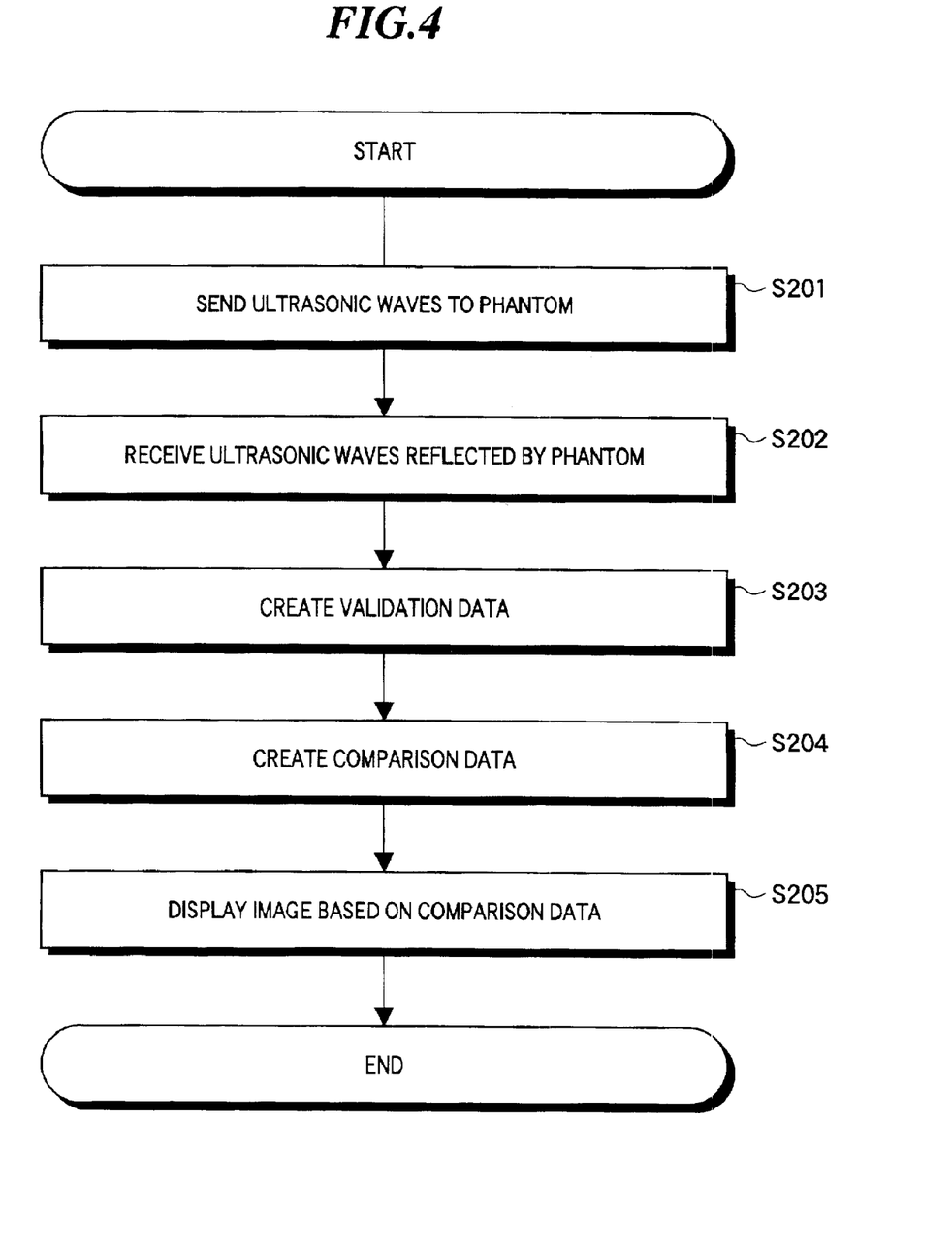
FIG. 4 is a flowchart showing the operation of checking the performance of the ultrasonic diagnostic apparatus according to the embodiment of the present invention.

The operation of checking performance of the ultrasonic diagnostic apparatus will then be described with reference to FIGS. 1 and 4. FIG. 4 is a flowchart showing operation of checking performance of the ultrasonic diagnostic apparatus. The performance checking operation is executed, for example, when an operator starts to use the ultrasonic diagnostic apparatus in every morning or when an operator judges that quality of images shown on the image display unit 45 is deteriorating.

The ultrasonic diagnostic apparatus 1 starts a series of performance checking operation as shown in FIG. 4 when an operator applies the ultrasonic probe 2 of the ultrasonic diagnostic apparatus 1 to the same phantom as used in the management data accumulation operation, and gives the ultrasonic diagnostic apparatus 1 a command to start the performance checking operation.

In the performance checking operation, the drive signal generating circuit 32 transmits a drive signal to the ultrasonic transmission unit 21 under control of the control unit 31, the ultrasonic transmission unit 21 transmits ultrasonic waves having the same transmission sound pressure or waveform as used in the management data accumulation operation to the phantom in accordance with the drive signal (Step S201). The ultrasonic waves transmitted from the ultrasonic transmission unit 21 are reflected by the phantom and are received by the ultrasonic detection unit 22 (Step S202).

In the ultrasonic detection unit 22, light having a specified wavelength generated by the light source unit 33 is modulated by the ultrasonic echoes reflected by the phantom. The direction in which the modulated light travels is changed by the beam separating unit 34, and the light passes through the focussing unit 35 and forms an image on the detection surface of the photodetecting unit 36.

The photodetecting unit 36 converts light received on the detection surface into an analog electric signal. The signal processing unit 37 conducts the specified signal processing on the analog electric signal output from the photodetecting unit 36. The A/D conversion unit 38 generates a digital signal from the analog electric signal output from the signal processing unit 37. The primary storage unit 39 stores the digital signal generated by the A/D conversion unit 38. The image processing unit 40 generates image data (hereinafter referred to also as "check data") by conducting the same image processing as used in the management data accumulation operation, on the digital signal stored in the primary storage unit 39. The check data prepared by the image processing unit 40 is stored in the secondary storage unit 41 (Step S203).

The data comparison unit 43 generates comparison data to compare the management data stored in the management data storage unit 42 with the check data stored in the secondary storage unit 41 (Step S204). More specifically, the data comparison unit 43 conducts processing of calculating a difference between the management data and the check data, division processing and other processing so as to generate comparison data indicating the results. The data comparison unit 43 may also generate comparison data for simply showing the management data and the check data in parallel or superposing them on the image display unit 45.

Figure 5A:
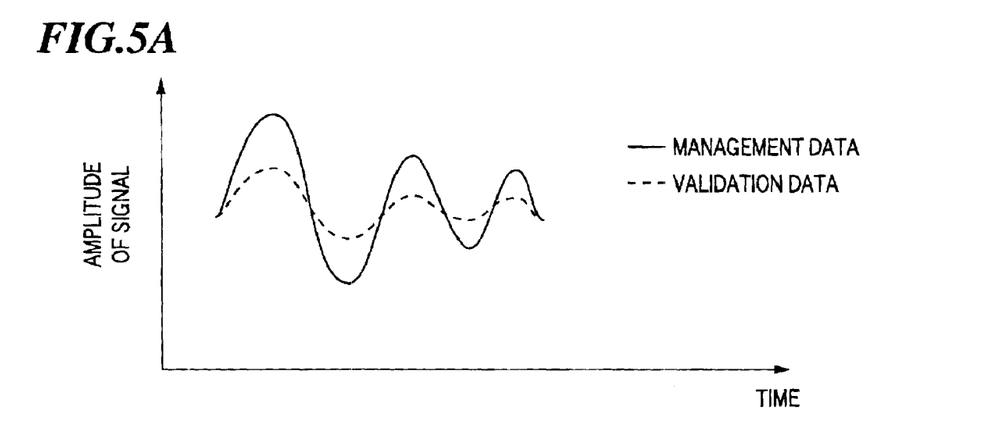
FIGS. 5A to 5C are diagrams showing examples of images displayed by the ultrasonic diagnostic apparatus according to the embodiment of the present invention.
Figure 5B:
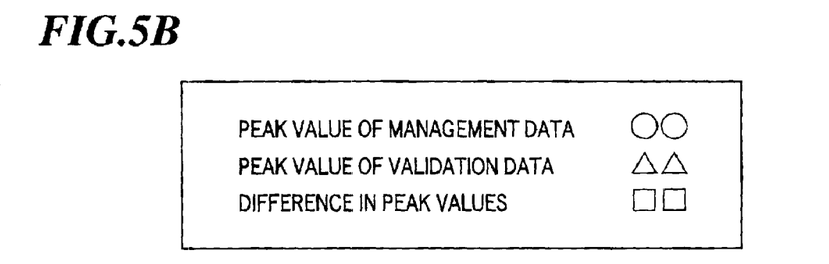
Figure 5C:
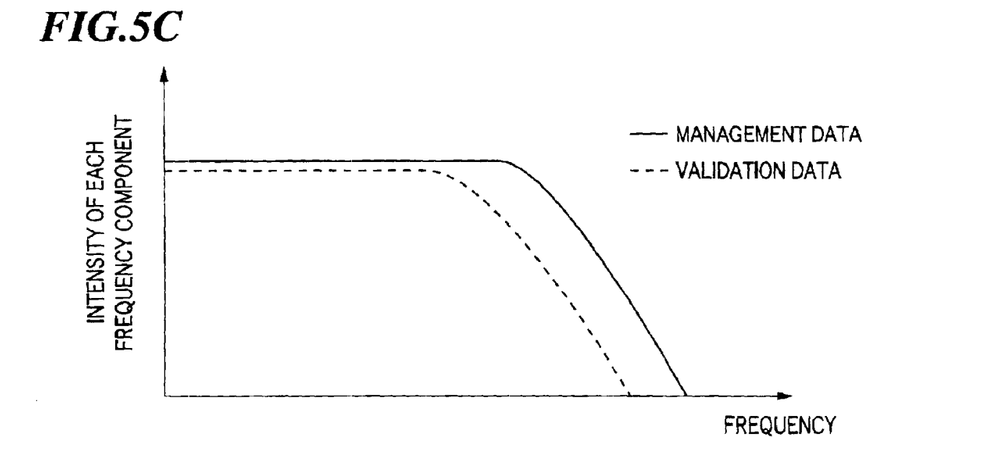

The image display unit 45 displays images on the basis of the comparison data generated by the data comparison unit 43 (Step S205). FIGS. 5A to 5C show an example of the images to be displayed on the basis of the comparison data. As shown in FIG. 5A, the respective waveforms of the management data and check data may be displayed. Alternatively, as shown in FIG. 5B, the characteristic values of the management data and the check data (for example, respective peak values of the management data and the check data which reflect information on a predetermined position of the phantom, or a difference between the respective peak values of the management data and the check data, etc.) may also be displayed. Alternatively, as shown in FIG. 5C, respective frequency characteristics of the management data and the check data (a frequency-gain diagram) may also be displayed.

In this embodiment, the management data and the check data obtained after image processing are used when the image quality checking operation is conducted. However, signals generated at any of the processing steps such as an RF signal, a signal after the logarithmic conversion, data after the A/D conversion, data after the image processing can also be used as signals for comparison. That is, the management data storage unit 42 and the secondary storage unit 41 may store data obtained from signals generated at any of the above processing steps, and the data comparison unit 43 make comparison on the basis of the stored data. Further, the management data storage unit 42 and the secondary storage unit 41 may store either the respective waveforms represented by the management data and the check data or their characteristic values such as peak intensity or frequency response obtained by analyzing the waveforms.

Figure 6A:
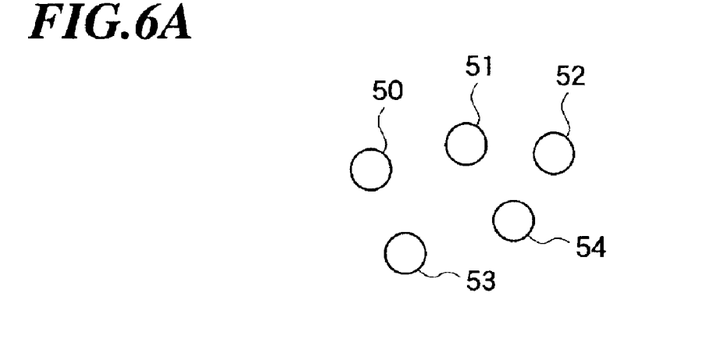
FIGS. 6A to 6C are diagrams showing examples of iron balls, etc. to be imaged by the ultrasonic diagnostic apparatus according to the embodiment of the present invention.
Figure 6B:
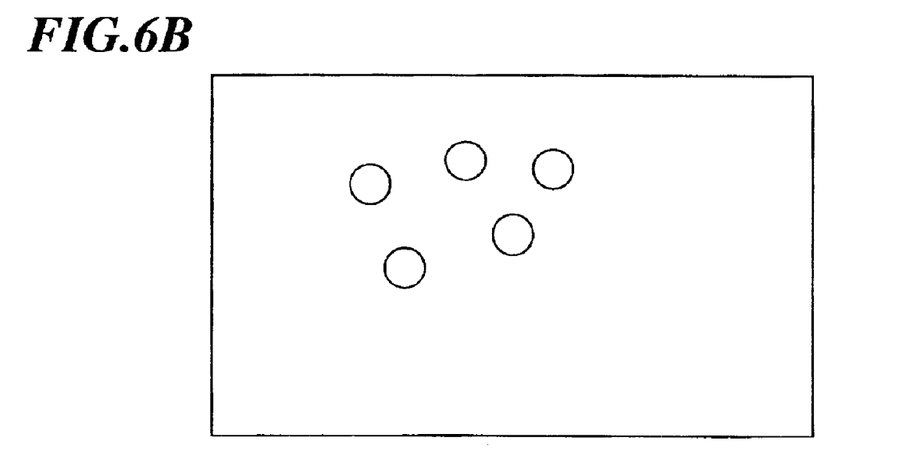
Figure 6C:
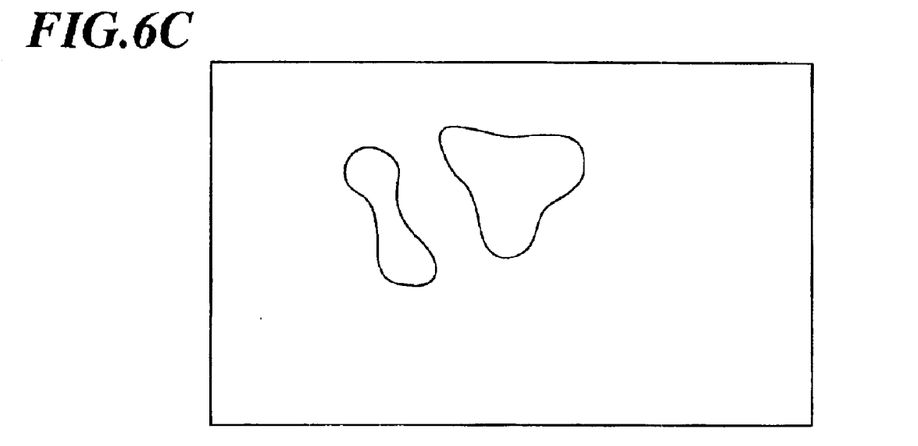

Also in this embodiment, a phantom is used to reflect ultrasonic waves when the management data accumulation operation and the performance checking operation are performed. In order to check the contrast, however, an object obtained by changing acoustic impedance step by step may be used. On the other hand, in order to check the resolution (direction resolution or distance resolution), an object containing a plurality of iron balls 50 to 54 which are arranged close to one another as shown in FIG. 6A may be used. If the resolution of the ultrasonic diagnostic apparatus 1 has not deteriorated, the images as shown in FIG. 6B would be obtained when the plurality of iron balls 50 to 54 are imaged. If the resolution has deteriorated, the images as shown in FIG. 6C would be obtained.

When the management data accumulation operation or the performance checking operation is performed, any of the one-dimensional, two-dimensional and three-dimensional scanning methods can be used to scan an object such as a phantom. Any image data obtained by the one-dimensional, two-dimensional and three-dimensional scanning can be used for comparison.

When an operator judges that the quality of images shown on the image display unit 45 has deteriorated and tries the ultrasonic diagnostic apparatus 1 to execute the above performance checking operation, no difference between the management data and the check data may possibly be found. This may be caused by the deterioration of the image display unit 45. In that case, the deterioration of the image display unit can be checked as follows:

(1) To Check Deterioration of Brightness (Gradation) of Image Display Unit 45

The operator makes the image display unit 45 display the specified low-contrast pattern on the basis of the image data retained by the reference pattern holding unit 44. The operator can check deterioration in brightness (gradation) of the image display unit 45 by viewing the displayed pattern.

Alternatively, the following method may also be used. The operator makes the image display unit 45 display the specified step pattern on the basis of the image data retained by the reference pattern holding unit 44. The image quality measuring unit 4 measures the brightness of step pattern displayed on the image display unit 45 to generate brightness data. The comparison data unit 43 generates comparison data on the basis of this brightness data and the initial brightness data previously obtained and stored in the management data storage unit 42. The operator can check deterioration in brightness (gradation) of the image display unit 45 by viewing an image displayed on the basis of the comparison data.

(2) To Check Deterioration of Resolution of Image Display Unit 45

The operator makes the image display unit 45 display the specified resolution measurement pattern on the basis of the image data retained by the reference pattern holding unit 44. The operator can check deterioration in resolution of the image display unit 45 by viewing the displayed pattern.

Alternatively, the following method may be used. The operator makes the image display unit 45 display the specified resolution measurement pattern on the basis of the image data retained by the reference pattern holding unit 44. The image quality measuring unit 4 images the resolution measurement pattern displayed on the image display unit 45 to generate imaging data. The comparison data unit 43 generates comparison data on the basis of this imaging data and the initial imaging data previously obtained and stored in the management data storage unit 42. The operator can check deterioration in resolution of the image display unit 45 by viewing an image displayed on the basis of the comparison data.

As set forth hereinabove, the present invention enables quantitative check of deterioration in quality of images displayed on an ultrasonic diagnostic apparatus, by comparing management data with check data or using the reference pattern. It is also possible to find out which causes the deterioration of image quality, the image display unit or the other parts.

While the illustrative and presently preferred embodiment of the present invention has been described in detail herein, it is to be understood that the inventive concepts may be otherwise variously embodied and employed and that the appended claims are intended to be construed to include such variations except insofar as limited by the prior art.

What is claimed is:

1. An ultrasonic diagnostic apparatus comprising:
   ultrasonic transmission means for transmitting ultrasonic waves;
   ultrasonic reception means for receiving ultrasonic echoes modulating light in accordance with the ultrasonic echoes and detecting the light so as to output detection signals;
   signal processing means for processing the detection signals output from said ultrasonic reception means to generate data;
   first storage means for storing the generated data as management data, said management data being obtained by transmitting ultrasonic waves to a predetermined object and receiving ultrasonic echoes reflected by said predetermined object;
   second storage means for storing the generated data as check data, said check data being obtained by transmitting ultrasonic waves to said predetermined object and receiving ultrasonic echoes reflected by said predetermined object when performance of said ultrasonic diagnostic apparatus is checked;
   comparison means for generating comparison data on the basis of both the management data stored in said first storage means and the check data stored in said second storage means; and
   an image display unit for displaying an image on the basis of the comparison data generated by said comparison means.

2. An ultrasonic diagnostic apparatus according to claim 1, further comprising:
   a control unit for controlling, when performance of said ultrasonic diagnostic apparatus is checked, said ultrasonic transmission means to transmit ultrasonic waves under the same conditions as used in obtaining the management data, said ultrasonic reception means to receive ultrasonic echoes under the same conditions as used in obtaining the management data, and said signal processing means to process the detection signals under the same processing conditions as used in obtaining the management data.

3. An ultrasonic diagnostic apparatus according to claim 1, wherein said comparison means generates comparison data for use in displaying at least one of (i) respective waveforms represented by the management data and the check data, (ii) respective peak values represented by the management data and the check data, (iii) the difference between the peak value represented by the management data and the peak value represented by the check data, and (iv) respective frequency characteristics represented by the management data and the check data.

4. An ultrasonic diagnostic apparatus according to claim 1, further comprising:
   third storage means for storing image data representative of a predetermined pattern for use in checking quality of said image display unit.

5. An ultrasonic diagnostic apparatus according to claim 4, further comprising:
   an imaging unit for tacking an image which is displayed on said image display unit on the basis of image data representative of said predetermined pattern.

6. A method of checking performance of an ultrasonic diagnostic apparatus, said method comprising the steps of:
   (a) previously transmitting ultrasonic waves to a predetermined object and receiving ultrasonic echoes reflected by said predetermined object, modulating light in accordance with the ultrasonic echoes and detecting the light to generate data and store the generated data as management data;
   (b) transmitting ultrasonic waves to said predetermined object and receiving ultrasonic echoes reflected by said predetermined object, modulating light in accordance with the ultrasonic echoes and detecting the light to generate data and store the generated data as check data when performance of said ultrasonic diagnostic apparatus is checked;
   (c) generating comparison data on the basis of both the management data stored at step (a) and the check data stored at step (b); and
   (d) displaying an image on the basis of the comparison data generated at step (c).

7. A method according to claim 6, wherein step (b) includes transmitting ultrasonic waves under the same conditions as used at step (a) and receiving ultrasonic echoes under the same conditions as used at step (a).

8. A method according to claim 6
   wherein each of steps (a) and (b) includes any one of two-dimensionally scanning said predetermined object and three-dimensionally scanning said predetermined object.

9. A method according to claim 6 wherein said predetermined object includes any one of an object having acoustic impedance, which is stepwise varied, and an object including a plurality of iron balls arranged therein.

10. A method according to claim 6, wherein step (c) includes generating comparison data for use in displaying at least one of (i) respective waveforms represented by the management data and the check data, (ii) respective peak values represented by the management data and the check data, (iii) the difference between the peak value represented by the management data and the peak value represented by the check data, and (iv) respective frequency characteristics represented by the management data and the check data.

11. A method according to claim 6, further comprising step of:
(e) displaying an image on the basis of image data representative of a predetermined pattern which is previously stored.

12. A method according to claim 11, further comprising steps of:
(f) generating image data by taking an image displayed at step (e); and
(g) comparing image data generated at step (f) with image data stored by previous taking an image displayed on the basis of said image data.

* * * * *